United States Patent [19]

Furusaki et al.

[11] Patent Number: 5,679,226
[45] Date of Patent: Oct. 21, 1997

[54] OXYGEN SENSOR

[75] Inventors: Keizo Furusaki; Tatsuya Okumura; Hideya Tanaka; Yasuhiro Yamada, all of Nagoya, Japan

[73] Assignee: NGK Spark Plug Co, Ltd., Nagoya, Japan

[21] Appl. No.: 528,500

[22] Filed: Sep. 14, 1995

[30] Foreign Application Priority Data

Sep. 19, 1994 [JP] Japan .................................. 6-251305

[51] Int. Cl.$^6$ .................................................. G01N 27/407
[52] U.S. Cl. .......................... 204/424; 204/427; 204/428
[58] Field of Search ...................................... 204/421–429

[56] References Cited

U.S. PATENT DOCUMENTS

| | | |
|---|---|---|
| 4,370,213 | 1/1983 | Oki et al. . |
| 4,556,475 | 12/1985 | Bayha et al. ............................. 204/427 |
| 4,609,454 | 9/1986 | Ziegler .................................... 204/427 |
| 4,923,587 | 5/1990 | Nishio et al. . |
| 5,049,255 | 9/1991 | Wolfe et al. . |
| 5,329,806 | 7/1994 | McClanahan et al. . |

FOREIGN PATENT DOCUMENTS

| | | |
|---|---|---|
| 0 132 691 | 7/1983 | European Pat. Off. . |
| 0 145 175 | 6/1985 | European Pat. Off. . |

Primary Examiner—T. Tung
Attorney, Agent, or Firm—Foley & Lardner

[57] ABSTRACT

An oxygen sensor includes a tubular metal shell, a tubular housing having an end attached to the metal shell and another end sealed by a seal member. A solid electrolyte tube is attached to the metal shell and has on inner and outer surfaces thereof electrode layers and lead layers connected to the electrode layers, respectively. A pair of lead wires extend through the seal member between inside and outside of a housing assembly constituted by the metal shell and housing while being sealingly held by the seal member. A pair of metallic leads are disposed inside of the housing assembly for connection between the lead layers and the lead wires, the metallic leads having at one end thereof electrode connecting portions having a spring property, the electrode connecting portions being attached to the inner and outer surfaces of the solid electrolyte tube and held in contact with the lead layers under spring pressure. A stopper is interposed between the seal member and the open end of the solid electrolyte tube so as to obstruct axial movement of the electrode connecting portions of the metallic leads relative to the solid electrolyte tube when the lead wires are pulled outward of the housing assembly.

3 Claims, 11 Drawing Sheets

OXYGEN SENSOR

BACKGROUND OF THE INVENTION

1. Field of the Invention

The present invention relates to an oxygen sensor used, for example, for detecting an oxygen content in the exhaust gases emitted from an internal combustion engine.

2. Description of the Prior Art

An oxygen sensor of this kind is made up of an oxygen content detecting element having a tubular shape with one end closed and made of solid electrolyte and a metallic housing assembly including a metal shell for holding the element thereon. The oxygen sensor is installed on an exhaust pipe of an internal combustion engine by way of the metal shell to bring an electrode layer (i.e., reference electrode layer) on the inner surface of the element in contact with a reference oxygen gas (i.e., atmospheric air) and an electrode layer (i.e., measurement electrode layer) on the outer surface of the element in contact with the exhaust gases. The oxygen sensor is adapted to cause an electromotive force (i.e., potential difference) between the electrodes in accordance with the difference of the oxygen content between the inner and outer surfaces of the element and output a signal representative of the electromotive force to a control circuit for thereby detecting the oxygen content in the exhaust gases and controlling the same.

The electrode layers formed on the inner and outer surfaces of the element of the oxygen sensor are connected by way of metallic leads to an output lead wire for connection to a control circuit and a grounding lead wire. The metallic leads have at one end thereof electrode connecting portions having a spring property. The electrode connecting portions are pushed axially of the element to fit in and on the element and held in contact with the lead layers under spring pressure. The metallic leads are connected at another end thereof to lead wires.

Figure 13:
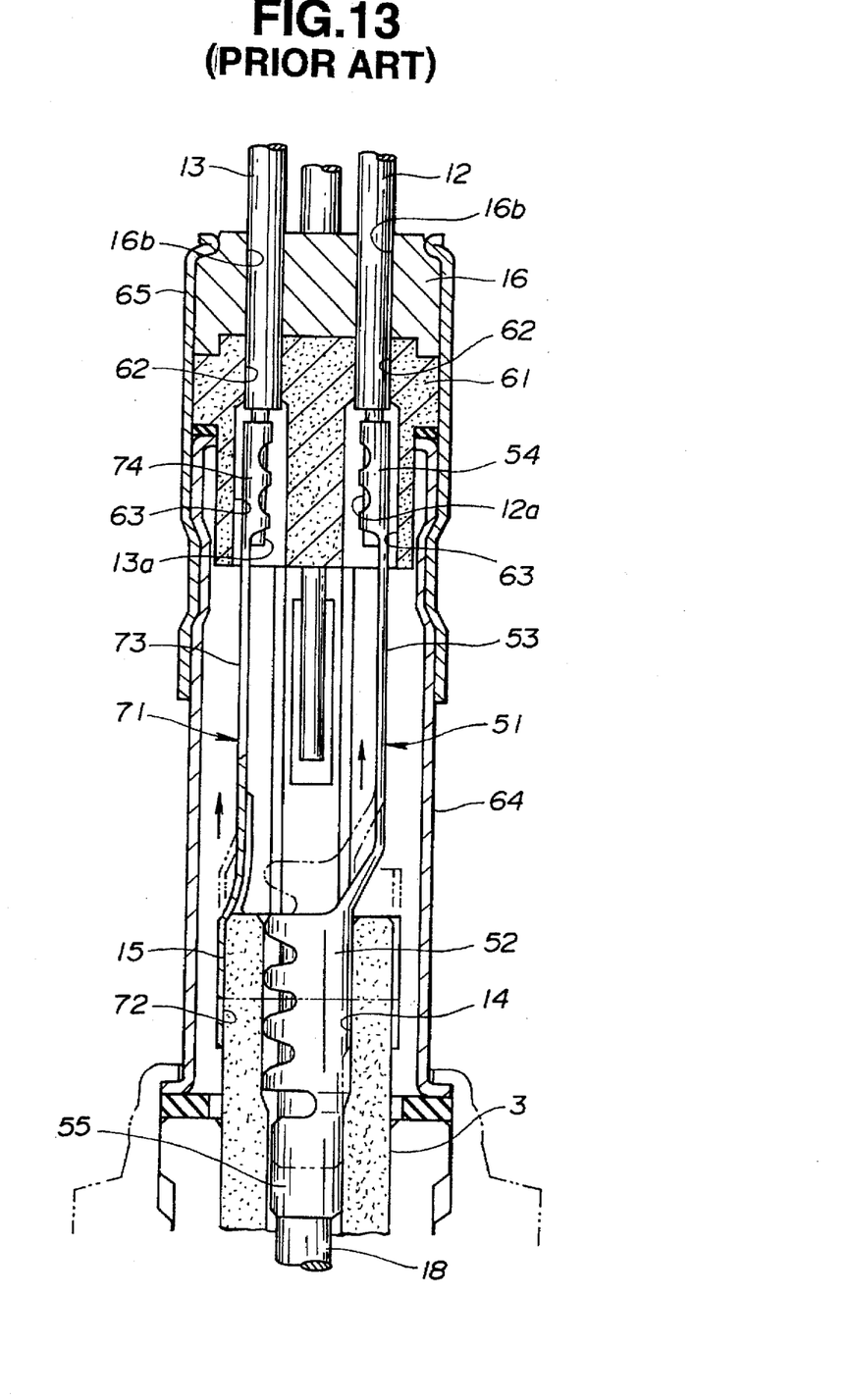
FIG. 13 is a view similar to FIG. 2 but shows a prior art oxygen sensor.
Figure 14:
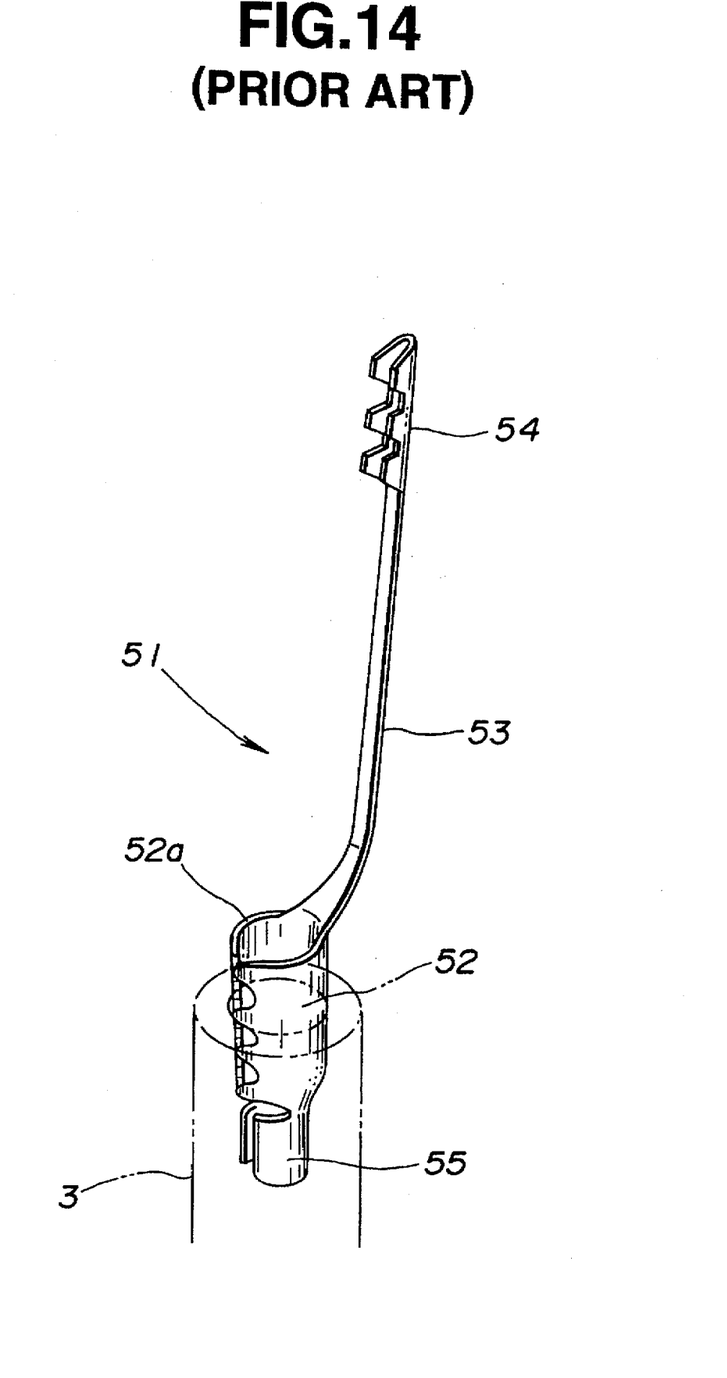
FIG. 14 is a perspective view of a metallic lead used in the prior art oxygen sensor of FIG. 13.

FIG. 13 shows a prior art oxygen sensor of the type utilizing metallic leads for connection between lead layers and lead wires. A metallic lead 51 is employed for connection between a lead layer 14 connected to an electrode layer on the inner surface of an oxygen content detecting element 3 and an output lead wire 12. The metallic lead 51 is constructed as shown in FIG. 14 and is formed from a metal plate having a spring property. The metallic lead 51 has an electrode connecting portion 52 at one end or lower end thereof. The electrode connecting portion 52 is formed into a tubular shape having a part-circular cross section. The electrode connecting portion 52 has, in an unloaded or unstressed state, an outer diameter that is a little larger than the inner diameter of the tubular lead layer 14 formed on the inner surface of the element 3. The metallic lead 51 further has a nearly vertical intermediate or stem portion 53 and a crimp-style terminal portion 54 of a U-like cross section at another end or upper end thereof. The crimp-style terminal portion 54 is provided for connection to lead wires. The intermediate portion 53 is provided between the electrode connecting portion 52 and the crimp-style terminal portion 54 for interconnecting therebetween. The electrode connecting portion 52 has a smaller diameter lower end portion for forming a ceramic heater gripping portion 55 of a part-circular cross section. The ceramic heater gripping portion 55 is smaller in diameter than the electrode connecting portion 52 and adapted to grip or hold a ceramic heater 18 under spring pressure. The ceramic heater gripping portion 55 has, in its unloaded or unstressed state, an inner diameter smaller than the outer diameter of the ceramic heater 18.

With such a metallic lead 51, the crimp-style terminal portion 54 is connected by crimping to an end portion 12a of a lead wire 12 extending through a sealing member 16, and the ceramic heater gripping portion 55 grips a heater 18. Under the above condition of the metallic lead 51, the electrode connecting portion 52 is pushed axially into the element 3 and brought in contact with the inner lead layer 14 under spring pressure or by spring force. In the meantime, 61 in FIG. 13 is an insulator made of a ceramic material, or the like and has a tubular shape or hollow cylindrical shape. The insulator 61 is arranged in contact with the bottom surface of the seal member 16 and has through holes consisting of smaller diameter through hole sections 62 aligned with respective through holes 16b of the seal member 16 and lower larger diameter through hole sections 63. By accommodating the crimp-style terminal portion 54 of the metallic terminal 51 within one of the through hole sections 63, the insulator 61 insulates the crimp-style terminal portion 54 of the metallic lead 51 from a crimp-style terminal portion 74 of a metallic lead 71 and metallic housing inner and outer tubes 64 and 65.

Figure 15:
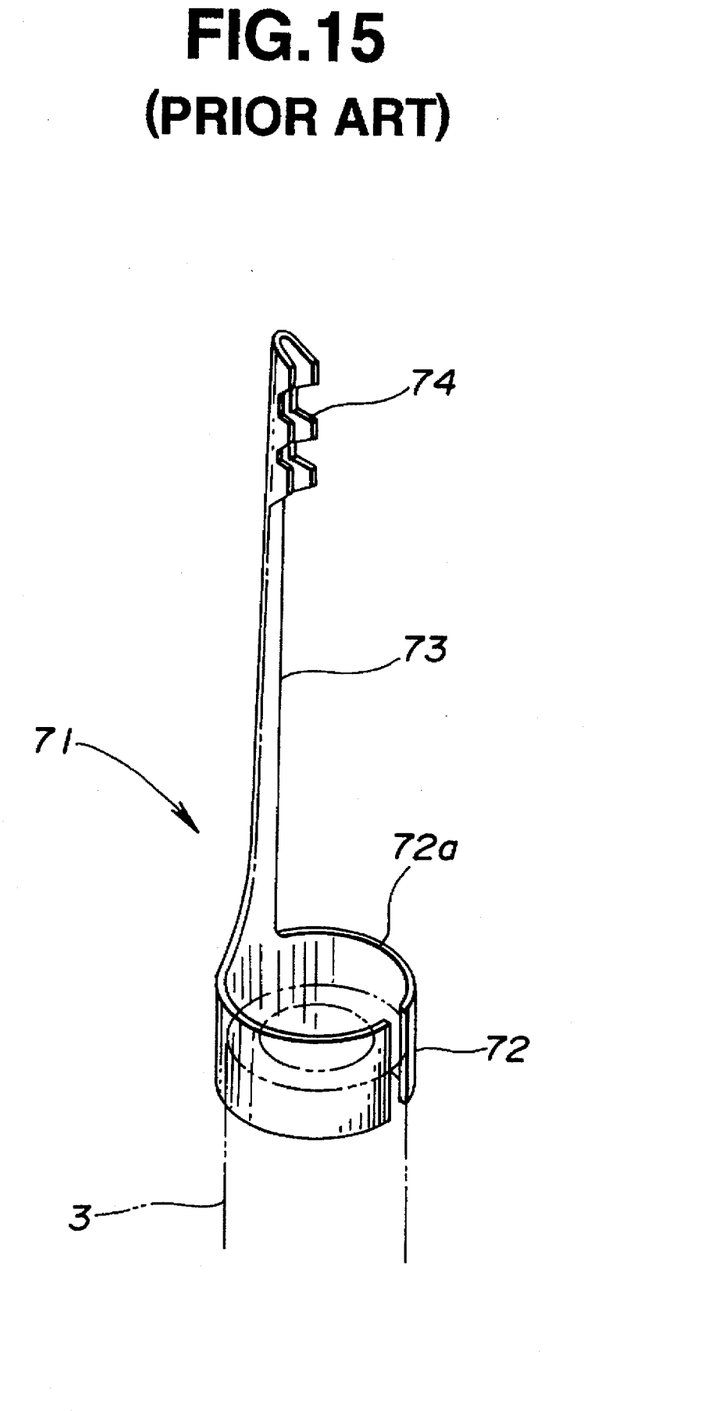
FIG. 15 is a perspective view of another metallic lead used in the prior art oxygen sensor of FIG. 13.

The metallic leads 71 is provided for connection between a lead layer 15 connected to an electrode layer on the outer surface of the element 3 and a grounding lead wire 13. The metallic lead 71 is constructed as shown in FIG. 15 and basically similar to the above described output metallic lead 51. That is, the metallic lead 71 is formed from a metal plate having a spring property and has an electrode connecting portion 72 at one or lower end thereof. The electrode connecting portion 72 is formed into a tubular shape having a part-circular cross section. The electrode connecting portion 72 has, in an unloaded or unstressed condition, an inner diameter smaller than the outer diameter of the tubular lead layer 15 formed on the outer surface of the element 3. The metallic lead 71 further has an intermediate or stem portion 73 and a crimp-style terminal portion 74 of a U-like cross section. The crimp-style terminal portion 74 is provided for connecting to the grounding lead wire 13 extending through the seal member 16. The intermediate portion 73 is provided between the electrode connecting portion 72 and the crimp-style terminal portion 74 for interconnecting therebetween. Under the condition of the crimp-style terminal portion 74 being connected to the inner end 13a of the grounding lead wire 13, the electrode connecting portion 72 is pushed axially of the element 3 to fit on the element 3 and is brought in contact with the lead layer 15 under spring pressure.

By the above structure, electrical connection between the metallic leads 51 and 71 and the electrode connecting portions 52 and 72 and attachment or fixing of them can be attained with ease since such electrical connection and attachment or fixing only requires to push the metallic leads 51 and 71 against the element 3 and make them fit in and on the open end of the element 3.

In such an oxygen sensor, the lead wires 12 and 13 may possibly be subjected to a tensile force even after installation of the sensor on an exhaust pipe for various reasons. The seal member 16 is thus required to not only sealingly surround the lead wires but fixedly hold the lead wires. However, the force exerted by the seal member for fixedly holding the lead wires is not sufficiently large. While in the prior art oxygen sensor, the insulator 61 is provided in contact with the seal member 16, such an insulator 61 can scarcely exert a force for obstructing axial movement of the lead wires.

For the above reason, the above described prior art oxygen sensor has a possibility that when the lead wires 12 and 13 are pulled outward by a relatively large force, the electrode connecting portions 52 and 72 connected to the inner and outer surface lead layers 14 and 15 of the element 3 are moved upward of the respective lead layers 14 and 15 as shown by the two-dot chain lines in FIG. 13 or may be separated from the element 3 in case the force is excessively large. Thus, the above described prior art oxygen sensor has a problem on the reliability and durability, i.e., a problem that unstable electrical connection and unstable outputting may occur or malfunction may occur due to disconnection by the separation, thus disabling accurate detection and control of oxygen content in the exhaust gases.

SUMMARY OF THE INVENTION

According to an aspect of the present invention, there is provided an oxygen sensor that comprises an oxygen content detecting element made of solid electrolyte and in the form of a circular tube with one end closed. Electrode layers are provided to inner and outer peripheral surfaces of the oxygen content detecting element, and a lead layer is provided to the oxygen content detecting element and connected to one of the electrode layers. A metallic lead having at one end thereof an electrode connecting portion having a spring property is provided, the electrode connecting portion being attached to the oxygen content detecting element and held in contact with the lead layer under spring pressure. The metallic lead is connected at another end thereof to a lead wire. A seal member sealingly holds the lead wire while allowing the same to extend outward thereof. A stopper is engaged with the electrode connecting portion of the metallic lead to prevent the electrode connecting portion from being separated from the lead layer when the lead wire is pulled outward to subject the metallic lead to a tensile force. By the above structure, even when the lead wire, which is connected to either of the lead layer on the inner surface of the oxygen detecting element or the lead layer on the outer surface of same, is pulled outward of the sensor to subject the metallic lead to a tensile force, the stopper effectively prevents the electrode connecting portion from being separated from the lead layer of the oxygen detecting element. Thus, the oxygen sensor of this invention enables the sensor to effect a stable operation in electrical conduction and outputting. As a result, the sensor of this invention can effect an improved accuracy in detection of oxygen content.

According to another aspect of the present invention, the stopper is interposed between the oxygen content detecting element and the seal member and has a hollow cylindrical portion surrounding the metallic lead radially thereof. By such a stopper, it becomes hard for liquid or gas to enter the inside of the oxygen content detecting element. For this sake, pollution of the reference oxygen sensor can be prevented with more efficiency, thus lowering of the accuracy in detection of oxygen content being prevented.

According to a further aspect of the present invention, the stopper is made of a ceramic material. This is desirable since it can effect an improved insulation of the metallic lead and an improved heat resistant property.

According to a further aspect of the present invention, there is provided an oxygen sensor comprising an oxygen content detecting element made of solid electrolyte and in the form of a circular tube with one end closed. Electrode layers are provided to inner and outer surfaces of the oxygen content detecting element and lead layers are provided to the inner and outer surfaces of the oxygen content detecting element and connected to the electrode layers, respectively. A pair of metallic leads having at one end thereof electrode connecting portions having a spring property are provided, the electrode connecting portions being attached to the oxygen content detecting element and held in contact with the lead layers under spring pressure, respectively. The metallic leads are connected at another end thereof to lead wires. A seal member sealingly holds the lead wires while allowing the same to extend outward thereof. A stopper is engaged with the electrode connecting portions of the metallic leads to prevent the electrode connecting portions from being separated from the lead layers when the lead wires are pulled to subject the metallic leads to a tensile force.

According to a further aspect of the present invention, there is provided an oxygen sensor comprising a tubular metal shell. A tubular housing is attached at one end thereof to the metal shell to constitute a housing assembly. A seal member is attached to another end of the tubular housing for sealingly closing the same. A solid electrolyte tube with one open is attached to the metal shell with the open end positioned inside of the housing assembly. Electrode layers are provided to inner and outer surfaces of the solid electrolyte tube and a lead layer is provided to the solid electrolyte tube and connected to one of the electrode layers. A lead wire extends through the seal member between inside and outside of the housing. While sealingly held by the seal member. The lead wire having an inner end is disposed inside of the housing. A metallic lead is disposed inside of the housing assembly for connection between the lead layer and the inner end of the lead wire, the metallic lead having at one end thereof an electrode connecting portion having a spring property. The electrode connecting portion is attached to one of the inner and outer surfaces of the solid electrolyte tube and is held in contact with the lead layer under spring pressure. A stopper is interposed between the seal member and the open end of the solid electrolyte tube and engaged with the electrode connecting portion to obstruct axial movement of the electrode connecting portion relative to the solid electrolyte tube when the lead wire is pulled outward of the housing assembly.

According to a further aspect of the present invention, the oxygen sensor further comprises a separator interposed between the sealing member and the stopper for insulating another end of the metallic lead relative to the housing assembly. The stopper is formed integral with or separately from the separator.

According to a further aspect of the present invention, the electrode connecting portion of the metallic lead has a part-circular cross section and has an axial end face flush with a face of the open end of the electrolyte tube. The stopper is hollow and cylindrical for allowing passage of the metallic lead therethrough and has an axial end abuttingly engaged with the open end of the solid electrolyte tube.

According to a further aspect of the present invention, the electrode connecting portion of the metallic lead is fitted on the open end of the solid electrolyte tube, the stopper having at the axial end a cross section including a four-cusped figure-like central opening for passage of the metallic lead, and a solid peripheral portion for abutting engagement with the axial end face of the electrode connecting portion.

According to a further aspect of the present invention, there is provided an oxygen sensor comprising a tubular metal shell, a tubular housing is attached at one end thereof to the metal shell. A seal member is attached to another end of the tubular housing for sealingly closing the same. A solid electrolyte tube with one open end is attached to the metal shell with the open end positioned inside of the housing assembly, the solid electrolyte tube having on inner and outer surfaces thereof electrode layers and lead layers connected to the electrode layers, respectively. A pair of lead wires extend through the seal member between inside and outside of the housing assembly while sealingly held by the seal member. The lead wires having inner ends are disposed inside of the housing. A pair of metallic leads are disposed inside of the housing for connection between the lead layers and the inner ends of the lead wires, the metallic leads having at one end thereof electrode connecting portions having a spring property. The electrode connecting portions are attached to the inner and outer surfaces of the solid electrolyte tube and are held in contact with the lead layers under spring pressure, respectively. A stopper is interposed between the seal member and the open end of the solid electrolyte tube and is engaged with the electrode connecting portions to obstruct axial movement of the electrode connecting portions relative to the solid electrolyte tube when the lead wires are pulled outward of the housing.

According to a further aspect of the present invention, the oxygen sensor further comprises a separator interposed between the sealing member and the stopper for insulating another end of the metallic leads relative to the housing assembly. The stopper is formed integral with or separately from the separator.

According to a further aspect of the present invention, each of the electrode connecting portions of the metallic leads has a part-circular cross section and has an axial end face flush with a face of the open end of the electrolyte tube. The stopper is hollow and cylindrical for allowing passage of the metallic leads therethrough and has an axial end abuttingly engaged with the open end of the solid electrolyte tube.

According to a further aspect of the present invention, the stopper has at the axial end a cross section including two circular openings for passage of the metallic leads, a radially inner solid portion for abutting engagement with the axial end face of one of the electrode connecting portions fitted in the open end of the solid electrolyte tube and a radially outer solid portion for abutting engagement with the axial end face of the other of the electrode connecting portions fitted on the open end of the solid electrolyte tube.

According to a further aspect of the present invention, the oxygen sensor further comprises a heater accommodated in the housing. A pair of lead wires are connected to the heater and extend between inside and outside of the housing through the stopper and the sealing member while sealingly held by the seal member. The stopper has at the above mentioned end a cross section including a four-cusped figure-like opening including a central opening section for disposition of the heater, a four-cusped figure section for disposition of the lead wires connected to the lead layers and the lead wires connected to the heater, a radially outer peripheral portion for abutting engagement with the axial end face of one of the electrode connecting portions fitted on the open end of the electrolyte tube, and four radially inwardly protruded portions for abutting engagement with the end face of the other of the electrode connecting portions fitted in the open end of the solid electrolyte tube.

According to a further aspect of the present invention, the stopper has a plurality of axial slits in such a manner as to allow the four cusped figure section opening radially outward so that the cross section of the stopper at the above mentioned end thereof consists of four independent solid portions.

The above structure is effective for solving the above noted problems inherent in the prior art device.

It is accordingly an object of the present invention to provide a novel and improved oxygen sensor that is highly reliable in operation and durable.

It is a further aspect of the present invention to provide a novel and improved oxygen sensor of the above described character that enables electrode connecting portions of metallic leads to be assuredly held in contact with lead layers of oxygen detecting element even when the lead wires are pulled outward of the sensor.

DETAILED DESCRIPTION OF THE PREFERRED EMBODIMENTS

Referring first to FIGS. 1 to 7, an oxygen sensor is generally indicated by 1 and shown as being of the type equipped with a ceramic heater, i.e., of the type having four lead wires. The oxygen sensor 1 includes a tubular metal shell 2 having a threaded portion 2a for attachment to an exhaust manifold or pipe of an internal combustion engine, and a tubular oxygen content detecting element or solid electrolyte tube 3 with one end closed and another end open. The solid electrolyte tube 3 has at a nearly longitudinal center thereof an outward flange 3a received inside the metal shell 2. The solid electrolyte tube 3 is fixedly attached to the metal shell 2 by interposing therebetween a tubular insulation member 4 made of a ceramic material, a seal member 5 made of powdered talc, a seal pipe 6, packings 7 and 8, and a housing inner tube 9 that cooperates with a housing outer tube 11 to constitute a tubular housing and further with the metal shell 2 to constitute a metallic housing assembly. The housing inner tube 9 is disposed at the rear end (i.e. the upper end in FIG. 1) of the metal shell 2 and has a flanged lower end 9a fixedly attached to the metal shell 2 by interposing between the packing 8 and a bent or crimped upper end 2b of the metal shell 2. By this arrangement, an insulation between the metal shell 2 and the solid electrolyte tube 3 can be attained, together with a seal between the metal shell 2 and the solid electrolyte tube 3 (i.e., between an exhaust gas side and a reference gas side) and a seal between the metal shell 2 and the housing inner tube 9 (i.e., air tight seal or liquid tight seal of the sensor 1). For attaining such a seal, the rear or upper end 2b of the metal shell 2 is bent so as to be laid over the lower end flange 9a of the housing inner tube 9 and crimped by pressing axially of the sensor 1. In the above manner, the solid electrolyte tube 3 is attached to the metal shell 2 with the open end thereof accommodated in the housing assembly constituted by the metal shell 2, the housing inner tube 9 and the housing outer tube 11. In the meantime, 10 is a protective cap attached to the front or lower end of the metal shell 2 for covering a portion of the solid electrolyte tube 3 protruding from the metallic housing assembly for thereby protecting the solid electrolyte tube 3.

Figure 1:
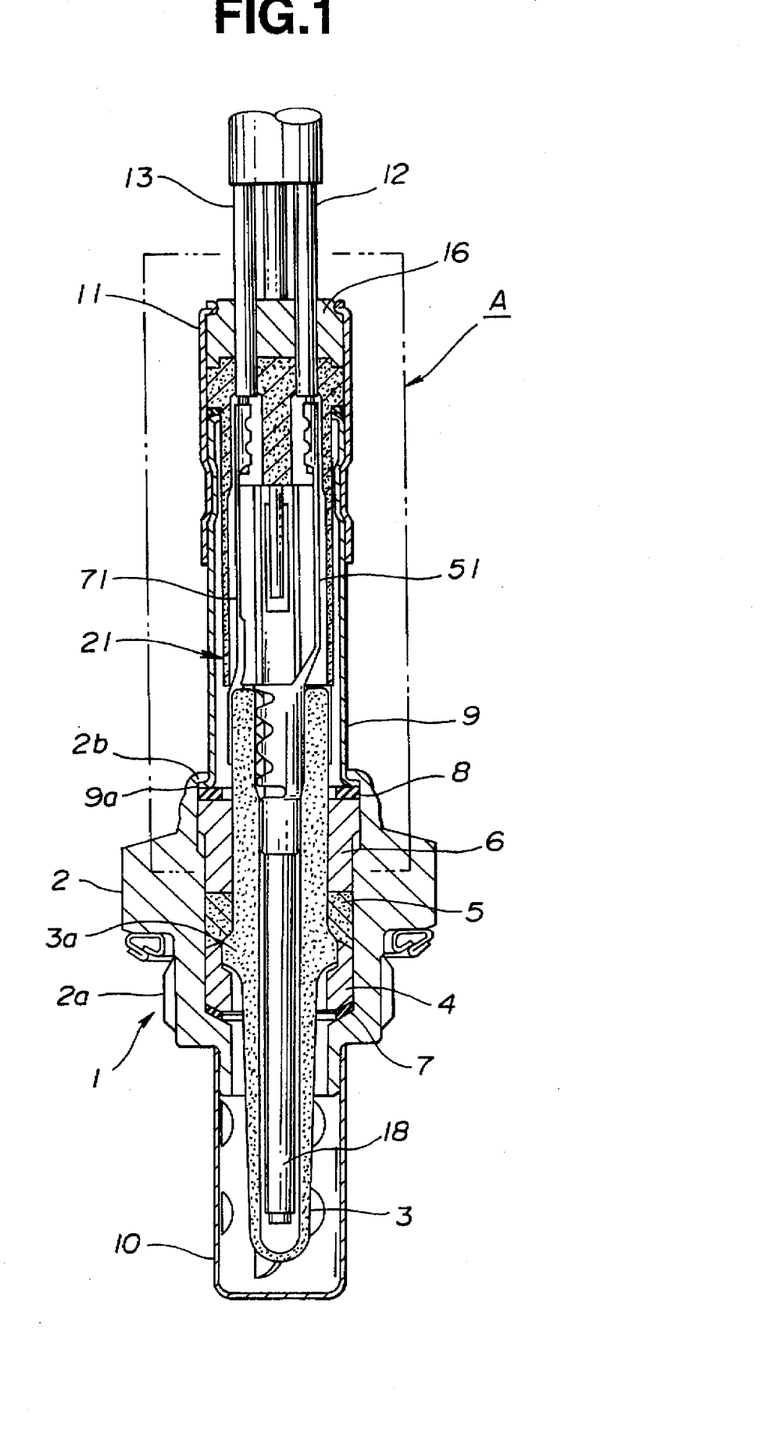
FIG. 1 is a longitudinal sectional view of an oxygen sensor according to an embodiment of the present invention.

The housing outer tube 11 is fitted on the upper end portion of the housing inner tube 9 to constitute the above described housing. An output lead wire 12 and a grounding lead wire 13 have inner ends disposed inside the housing and connected to an inner surface lead layer 14 and an outer surface lead layer 15 by way of the same metallic leads 51 and 71 as those shown in FIGS. 14 and 15. The lead layers 14 and 15 are formed on the inner and outer surfaces of the solid electrolyte tube 3 at a location adjacent the open end of the solid electrolyte tube 3. The lead layers 14 and 15 are connected to the electrode layers 3b and 3c formed on the inner and outer surfaces of the solid electrolyte tube 3, respectively. The metallic leads 51 and 71 have at one end thereof electrode connecting portions 52 and 72 for connection to the inner surface lead layer 14 and the outer surface lead layer 15 and at another end crimp-style terminal portions 54 and 74 for connecting to the lead wires 12 and 13. The electrode connecting portions 52 and 72 are respectively pushed against the open end of the solid electrolyte tube 3 and fitted in and on the inner surface lead layer 14 and the outer surface lead layer 15 of the solid electrolyte tube 3 in such a manner that upper end faces 52a and 72a of the electrode connecting portions 52 and 72 are flush with the face of the open end or upper end of the solid electrolyte tube 3. The lead wires 12 and 13 have inner ends 12a and 13a disposed inside of the housing and connected to the crimp-style terminal portions 54 and 74 of the metallic leads 51 and 71. The lead wires 12 and 13 extend outward of the housing through a seal member 16 whilst being sealingly held by the seal member 16. In the meantime, indicated by 17 is a pair of lead wires, though only one is shown in FIG. 1, which is connected to a ceramic heater 18 for heating the solid electrolyte tube 3. The lead wires 17 extend outward of the housing through the seal member 16 while sealingly held by the seal member 16. The seal member 16 is attached to the upper end of the housing outer tube 11 to sealingly close the same. The seal member 16 is in the form of a disc and has a recess 16a at a nearly central portion of its bottom. The seal member 16 has four axial through holes 16b for allowing passage of the lead wires 12, 13 and 17 therethrough. The through holes 16b are arranged in a circular array with equal intervals. It is desirable to form the seal member 16 of a fluorine resin having a high heat resistant property. In this embodiment, the seal member 16 is made of PFA (tetrafluoroethylene-perfluoroalkyvinylester).

An important feature of the present invention resides in a stopper 21, which will now be described. The stopper 21 has a hollow cylindrical body 30 hanging from a lower end of a separator 22. That is, the stopper 21 in this embodiment is formed integral with the separator 22 to constitute a single piece.

Figure 4A:
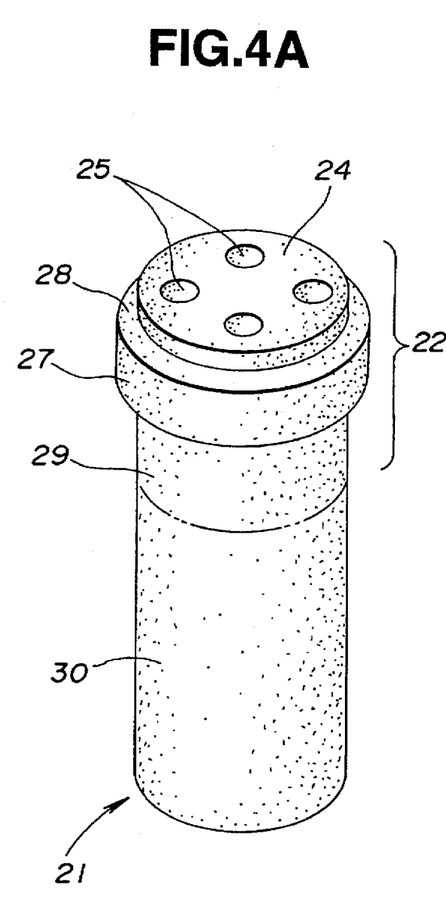
FIG. 4A is a perspective view of the stopper of the oxygen sensor of FIG. 1 when observed from above.
Figure 4B:
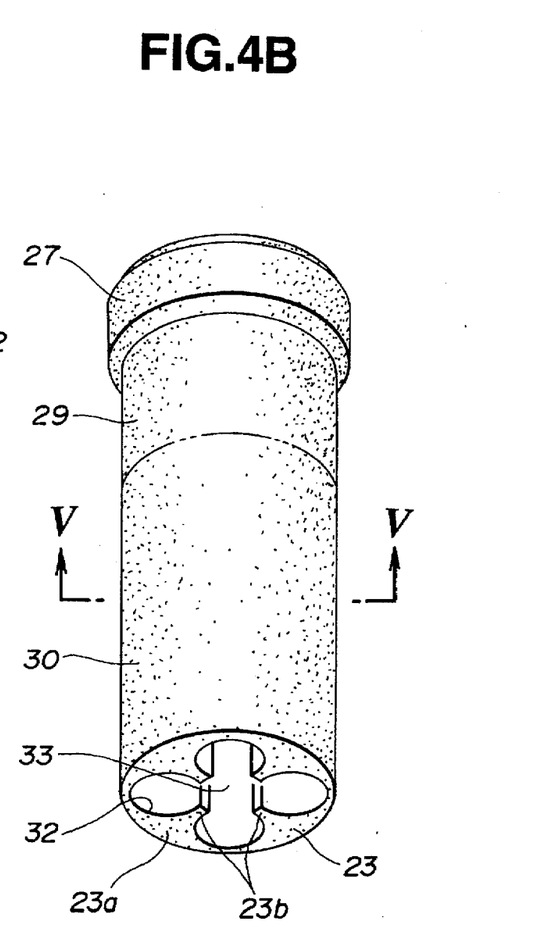
FIG. 4B is a perspective view of the stopper of the oxygen sensor of FIG. 1 when observed from below.
Figure 5:
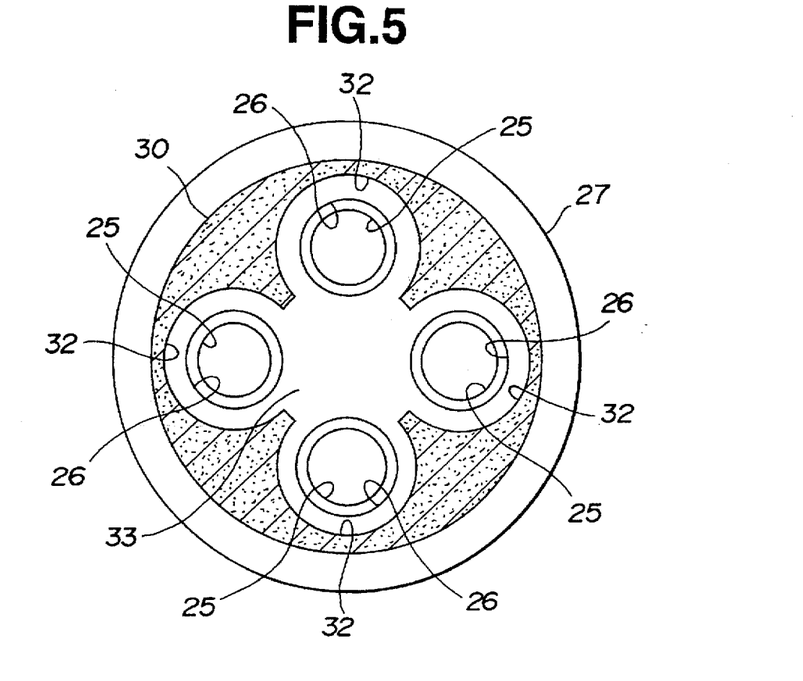
FIG. 5 is an enlarged sectional view taken along the line V—V in FIG. 4B.
Figure 6:
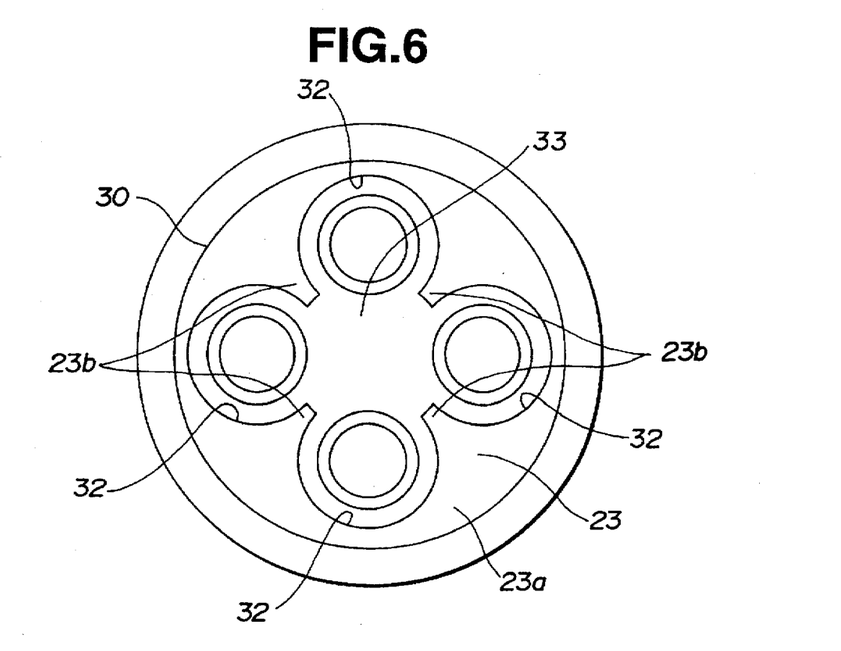
FIG. 6 is an enlarged bottom plan view of the stopper of FIG. 1.

In FIGS. 4A and 4B, the portion above the two-dot chain line represents the separator 22. The separator 22 is similar to that of the above described prior art oxygen sensor and made of a ceramic material. The separator 22 has an upper end 24 fittingly engaged in the recessed bottom of the seal member 16. The separator 22 is in the form of a disc and adapted to fit at an upper end 24 in the recess 16a of the seal member 16. The separator 22 has four stepped through holes axially aligned with the through holes 16b of the seal member 16 and includes upper smaller diameter through hole sections 25 and lower larger diameter through hole sections 26. The larger diameter through hole sections 26 are adapted to accommodate therewithin the crimp-style terminal portions 54 and 74 of the metallic leads 51 and 71 to connect thereto the inner ends 12a and 13a of the lead wires 12 and 13, respectively. The separator 22 has at a location adjacent the upper end thereof an outward flange 27 having an upper end face 28 brought into abutting engagement with the bottom face of the seal member 16. The separator 22 has at a location axially under the flange 27 a hollow cylindrical portion 29 of the same outer diameter as the hollow cylindrical body 30.

The stopper 21 has a lower end face 23 in abutting engagement with the upper end faces 52a and 72a of the electrode connecting portions 52 and 72 of the metallic leads, i.e., in abutting engagement with the face of the open end of the solid electrolyte tube 3. The stopper 21 further has a through hole consisting of axial hole sections 32 larger in diameter than the through hole sections 26 and axially aligned with the same, respectively and a center hole section 33 concentric with the hollow cylindrical body 30. Thus, the stopper 21 of this embodiment has at the lower end thereof a cross section including a four-cusped figure-like opening including a central opening section 33 for disposition of the ceramic heater 18, a four-cusped figure section for disposition of the metallic leads 51 and 71 connected to the lead layers 14 and 15 and the metallic leads 18b connected to the ceramic heater 18, a radially outer peripheral portion 23a for abutting engagement with the axial end face 72a of the electrode connecting portion 72 fitted on the open end of the solid electrolyte tube 3, and four radially inwardly protruded portions 23b for abutting engagement with the end face 52a of the electrode connecting portion 52 fitted in the open end of the solid electrolyte tube 3.

Figure 7:
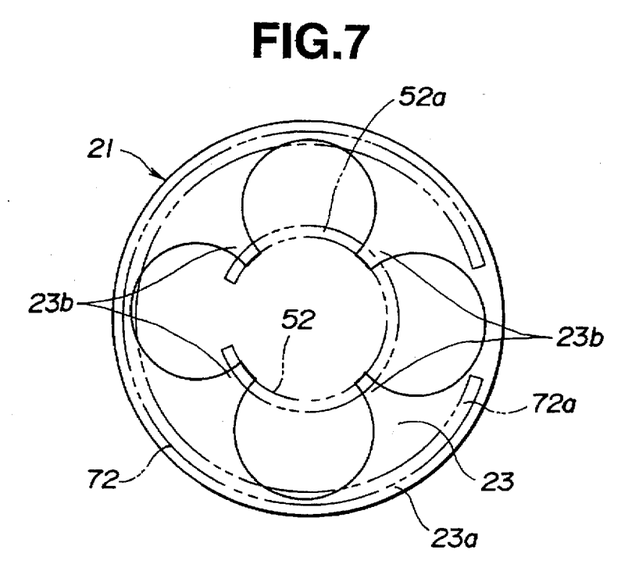
FIG. 7 is a view similar to FIG. 6 but shows how the stopper of FIG. 1 engages upper end faces of electrode connection portions of metallic leads.

In the oxygen sensor 1, when the lead wires 12 and 13 are pulled to subject the electrode connecting portions 52 and 72 of the metallic leads 51 and 71 to a tensile force so that the electrode connecting portions 52 and 72 are urged for removal or separation from the lead layers 14 and 15, axial movements of the electrode connecting portions 52 and 72 are stopped or blocked by the lower end face 23 of the stopper 21 so that separation or removal of the electrode connecting portions 52 and 72 from the lead layers 14 and 15 is prevented. Furthermore, as shown in FIG. 7, the outer peripheral part 23a of the lower end face 23 of the stopper 21 is engaged almost at its entirety with the upper end face 72a of the electrode connecting portion 72 connected to the outer surface lead layer 15, whereas the four radially inwardly protruded portions 23b are engaged, with equal intervals, with the upper end face 52a of the electrode connecting portion 52 connected to the inner surface lead layer 14 so that each radially inwardly protruded portions 23b effect an equal blocking action. Accordingly, inclination of the electrode connecting portions 52 and 72 does not occur, thus making it possible to obtain stable and assured conduction between the electrode connecting portions 52 and 72 and the lead layers 14 and 15.

Further, the stopper 21 with the hollow cylindrical body 30 is adapted to surround the metallic leads 51 and 71 radially whereof and at a location between the open end of the solid electrolyte tube 3 and the crimp-style terminal portions 54 and 74 of the metallic leads 51 and 71, and the lower end face 23 of the stopper 21 is adapted to be matched with or joined with the open end face of the solid electrolyte tube 3. By this arrangement, even if deterioration occurs in the seal between the solid electrolyte tube 3 and the lower part of the metal shell 2, thus allowing oil, water, exhaust gases or gasoline to intrude into the inside of the housing inner tube 9, it is difficult for such liquid and gas to further intrude into the inside of the oxygen sensor 1 due to the provision of the stopper 21 so that the reference oxygen gas (open air) does not become polluted or contaminated. Accordingly, the oxygen sensor 1 can prevent deterioration of the oxygen content detecting ability and corrosion of the inner surface electrode layer 14 and can effect a reliable operation for an elongated period.

The oxygen sensor 1 is assembled as follows.

Firstly, the solid electrolyte tube 3 and the housing inner tube 9 are fixed to the metal shell 2 to prepare a front end side subassembly.

On the other hand, the ends 12a and 13a of the lead wires 12 and 13 are connected to the inner face and outer face lead layers 14 and 15 of the solid electrolyte tube 3 by way of the metallic leads 51 and 71 in the following manner. That is, the end 12a of the output lead wire 12 is let to pass through the through hole 16b of the seal member 16 and the through holes 25, 26 and 32 of the separator 22 and the stopper 21. The end 12a of the lead wire 12 is then connected by crimping to the crimp-style terminal portion 54 of the metallic lead 51. The ceramic heater 18 is gripped by the heater gripping portion 55. The end 13a of the grounding lead wire 13 is let to pass similarly through the through hole 16b of the seal member 16 and the through holes 25, 26 and 32 of the separator 22 and the stopper 21 and is connected by crimping to the crimp-style terminal portion 74 of the metallic lead 71. The end portions of a pair of lead wires 17 connected to the ceramic heater 18 are let to pass through the through holes 16b of the seal member 16 and the through holes 25, 26 and 32 of the separator 22 and the stopper 21 and connected by soldering to the connecting terminals 18a of the heater 18 by way of intermediate metallic leads 18b. The thus obtained assembly is fitted in the housing outer tube 11 previously installed on the lead wire side in such a manner that the seal member 16 is abuttingly engaged with the upper bent end 11a of the housing outer tube 11 for thereby sealingly closing the same and the upper end 24 of the stopper 21 is fittingly engaged in the recess 16a of the seal member 16, whereby a rear end side subassembly is prepared.

Then, the rear end side subassembly and the front end side subassembly are assembled in such a manner that the housing outer tube 11 is fitted on the housing inner tube 9 and the electrode connecting portions 52 and 72 are pushed axially into and onto the open end of the solid electrolyte tube 3 so as to be brought in contact with the inner face and outer face lead layers 14 and 15 under spring pressure and thereby electrically connected to same. The upper end portion of the above described housing outer tube 11 is pressed axially by a predetermined compression force and heated to a predetermined temperature so that the seal member 16 is deformed so as to seal the interface between the lead wires 12, 13 and 15 and the seal member 16, and the lower end portion of the housing outer tube 11 and the inner tube 9 are driven inward so as to reduce in diameter and thus joined together by caulking. In the meantime, a packing 34 made of fluororesin is disposed between the lower face of the flange 27 of the separator 22 and the upper end portion of the inner tube 9 to provide a seal therebetween. In the prior sensor as shown in FIG. 13, there is not provided between the separator 61 and the electrode connecting portions 52 and 72 any structure for transmitting a pushing force therebetween. Thus, in order to push each electrode connecting portions 52 and 72 into the respective lead layers 14 and 15, a particular metallic jig for assemblage is used to insert the electrode connecting portions 52 and 72 into the housing inner tube 64 and thereafter the separator 61 and the seal member 16 are installed in sequence. In contrast to this, in this embodiment, the stopper 21 can transmit a pushing force for pushing the electrode connecting portions 52 and 72 against the respective lead layers 14 and 15. By previously assembling the seal member 16, the stopper 21 and the metallic leads 51 and 71 into a single unit so that they are inserted into the inner tube 9 all at once, it becomes possible to push the electrode connecting portions 52 and 72 into the respective lead layers 14 and 15 located at the innermost part of the housing inner tube 9 without using a particular jig. Accordingly, the oxygen sensor 1 of this embodiment can effect easier assemblage.

In the foregoing, it is to be noted that the stopper 21 is not limited to what has been described and shown in the above embodiment. For example, the stopper 21 can be designed to have another shape and structured so long as it is held engaged with the electrode connecting portions 52 and 72 and prevents them from being separated from the lead layers 14 and 15 of the solid electrolyte tube 3 when the lead wires 12 and 13 are pulled outward to subject the metallic leads 51 and 71 to a tensile force. Accordingly, although an action of preventing, in case oil or the like enters into the housing inner tube 9, such oil or the like from intruding further into the inside of the oxygen sensor 1 as is obtained in the above described embodiment, is eliminated, slits 35 may be formed in the cylindrical body 30 of the stopper 21 in the above described embodiment with suitable intervals. By the provision of the slits 35, the sensor can be made lighter. In this connection, the stopper 21 in FIG. 8 has a plurality of axial slits 35 in such a manner as to allow the four-cusped figure section 32 to open radially outward so that the cross section of the stopper 21 at the lower end thereof consists of four independent solid portions.

Figure 9:
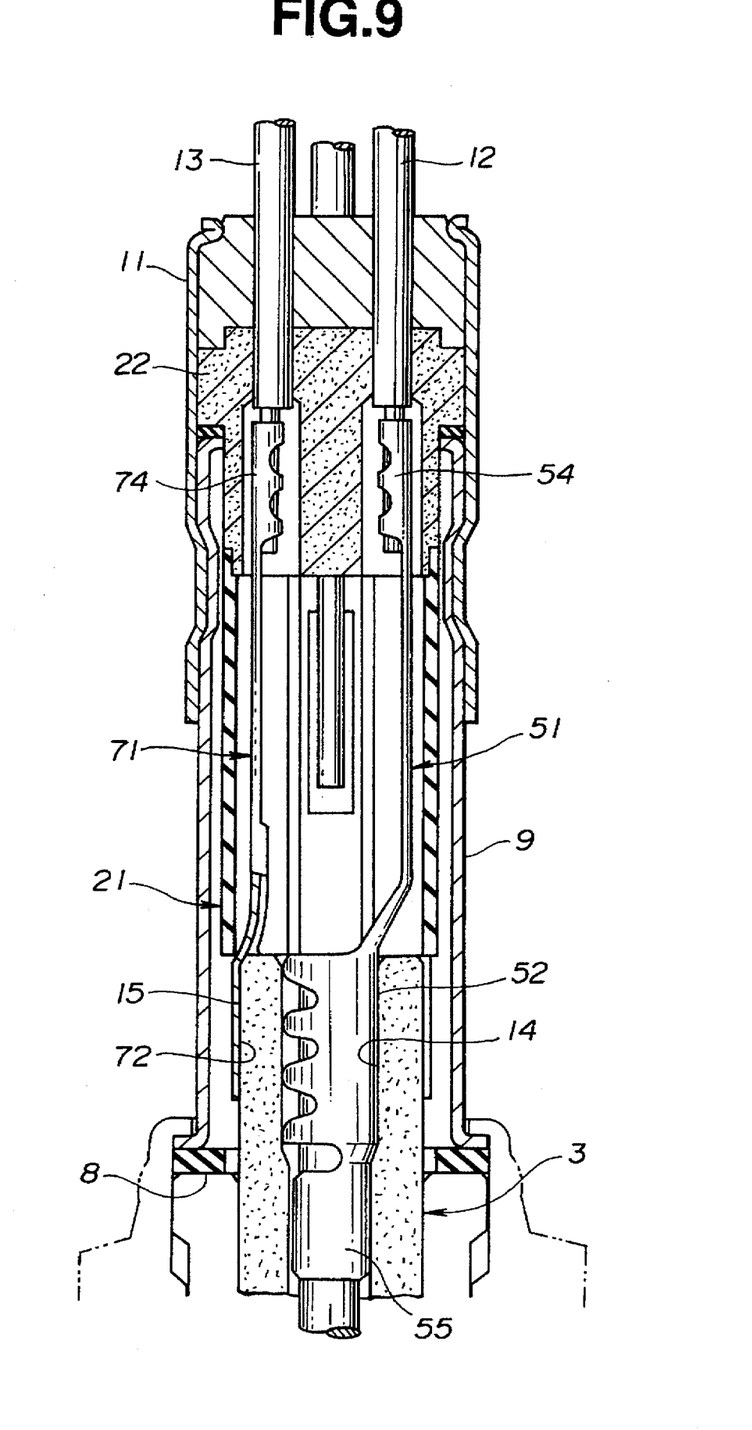
FIG. 9 is a view similar to FIG. 2 but shows a further variant of the stopper.

Further, while in the above described embodiment the stopper 21 is formed integral with the separator 22, they can be separated in the place indicated by the two-dot chain line in FIG. 4 so that the separator 22 and the stopper 21 are formed separately from each other as shown in FIG. 9. In FIG. 9, the lower end outer portion of the separator 22 is formed into a stepped shape and the upper end inner circumferential portion of the stopper 21 is stepped correspondingly so that they can be fitted together. Except for this, the stopper 21 and separator 22 are the same as that shown in FIG. 2 so similar reference characters are used to indicate similar parts and portions.

Figure 2:
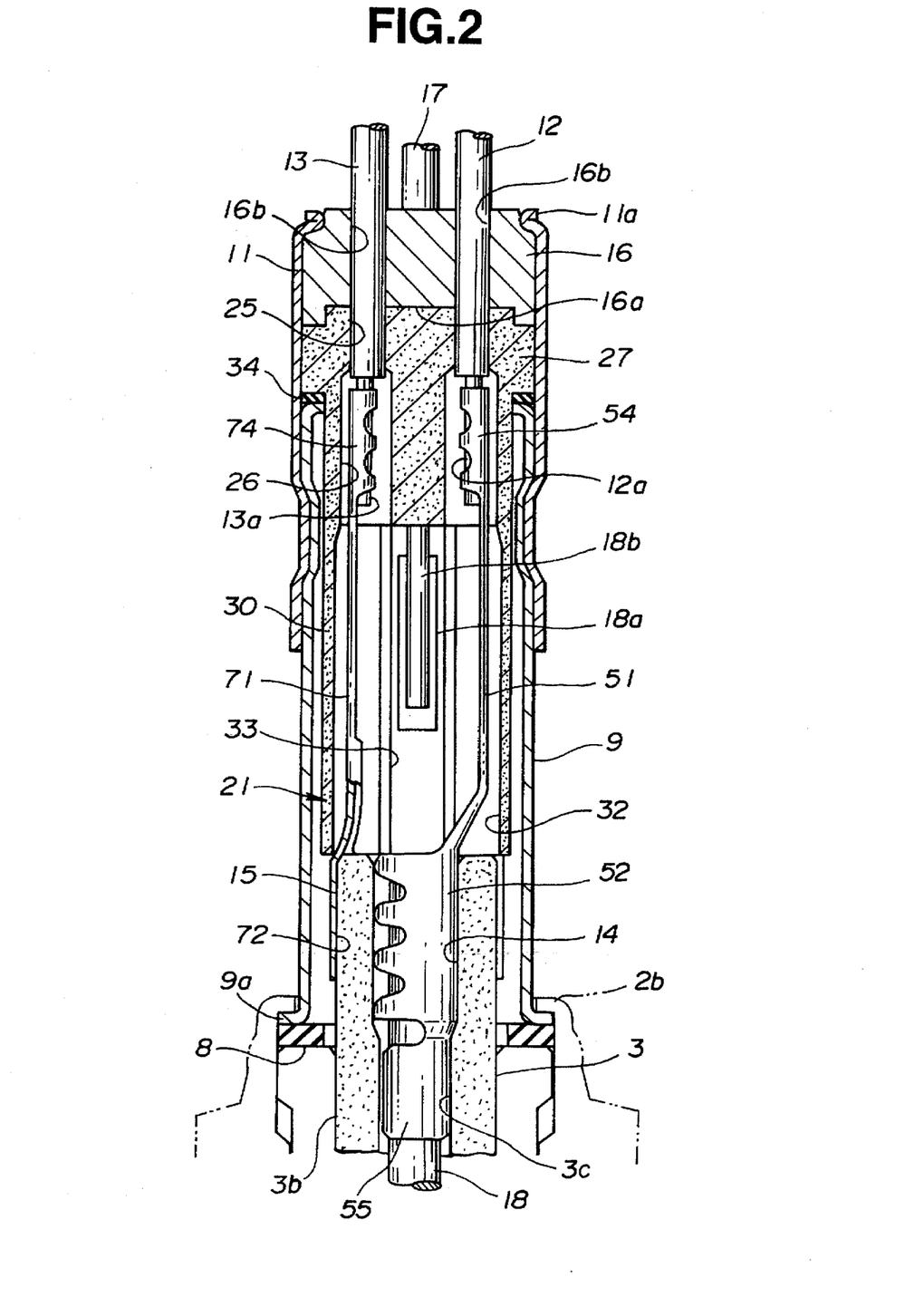
FIG. 2 is an enlarged view of a portion "A" of FIG. 1.
Figure 3:
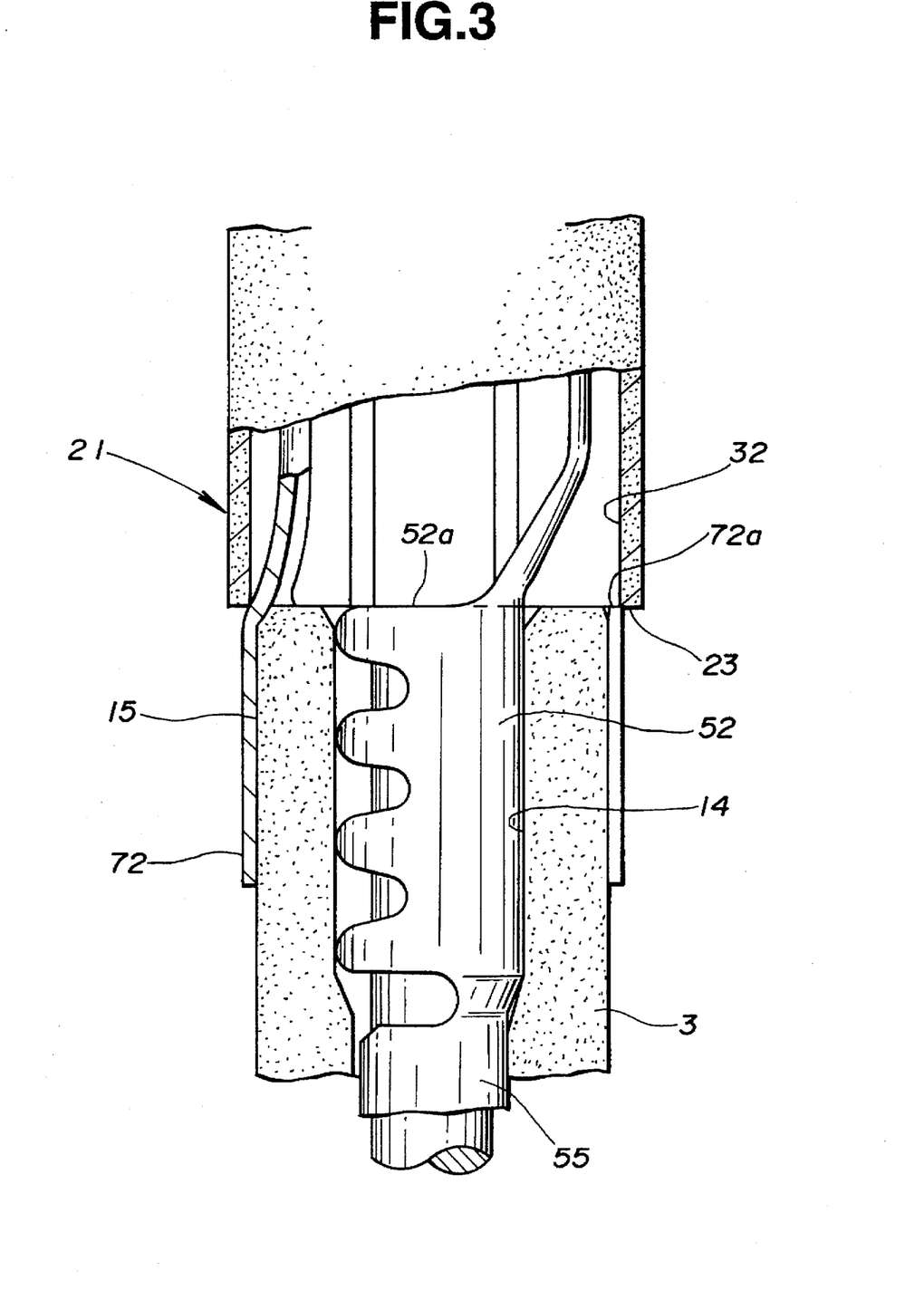
FIG. 3 is a fragmentary enlarged view of the oxygen sensor of FIG. 1 and illustrates a stopper in a state of being abuttingly engaged with ends of electrode connecting portions of metallic leads.
Figure 8:
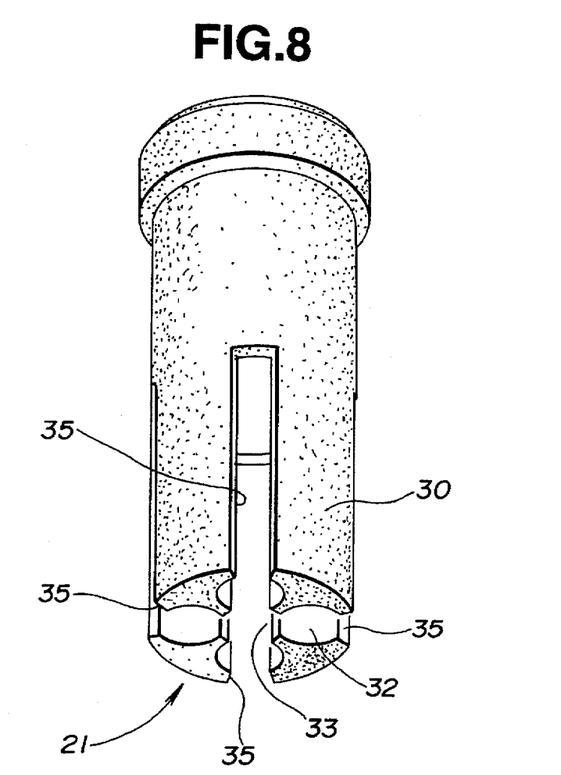
FIG. 8 is a view similar to FIG. 4B but shows a variant of the stopper.
Figure 10:
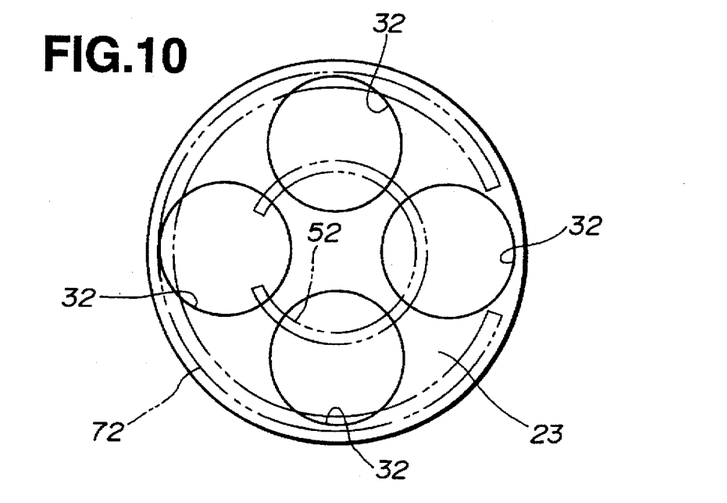
FIG. 10 is a view similar to FIG. 7 but shows a further variant of the stopper.
Figure 11:
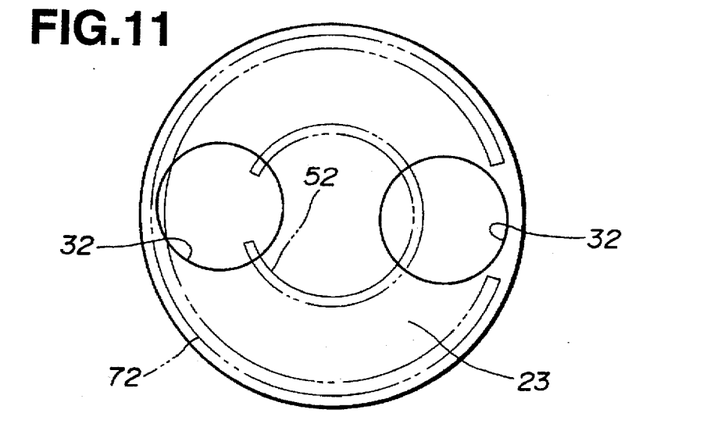
FIG. 11 is a view similar to FIG. 7 but shows a further variant of the stopper.

Further, in the foregoing, the oxygen sensor 1 has been described and shown as being of the type having four leads, i.e., a pair of output and grounding lead wires 12 and 13 connected by way of the metallic leads 51 and 71 to the inner surface and outer surface lead layers 14 and 15 and a pair of lead wires 17 for the ceramic heater 18. However, this is not for the purpose of limitation but the oxygen sensor can be of the type not equipped with any heater, i.e., of the type having two leads, which is constructed so as to dispense with such a ceramic heater 18, intermediate lead 18b, lead wires 17, and the gripping portion 55 of the metallic lead 51 otherwise provided to the above described embodiment. However, in such a case, the above described seal member 16 needs to be of such a variant that does not have any through holes for the lead wires 17. In the meantime, regarding the stopper 21, while such one as shown in FIGS. 2, 8 or 9 can be used as it is, it can be of such a variant as for example shown in FIG. 10, i.e., can be of such a variant that has a lower end face (the face for engagement with the electrode connecting portion of each metallic lead) 23 having only four through holes 32. Further, as shown in FIG. 11, the stopper can be of such one that has two through holes 32. In the meantime, in FIGS. 10 or 11, two-dot chain lines indicate the upper ends of the electrode connecting portions 52 and 72.

Figure 12:
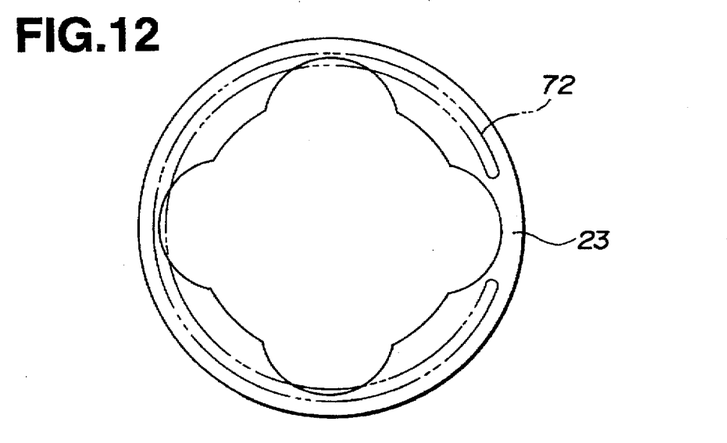
FIG. 12 is a view similar to FIG. 7 but shows a further variant of the stopper.

Further, in the foregoing, the oxygen sensor can be of the three lead type or of a so-called case grounded type in which the inner surface lead layer 14 of the solid electrolyte tube 3 is electrically connected to the output lead wire 12 for thereby being connected to a control circuit whilst the outer surface electrode layer 15 of the solid electrolyte tube 3 is electrically connected to the metallic housing assembly for thereby being grounded by way of the exhaust pipe. That is, the oxygen sensor can be of the type in which the lead layer (normally, outer surface lead layer) connected to one of the inner surface and outer surface electrode layers of the solid electrolyte tube is adapted to be grounded by way of the exhaust pipe and the lead layer connected to the other of the electrode layers is connected to the metallic lead which is in turn connected to the output lead wire. In the meantime, in such a case, it will suffice to prevent only the metallic lead for connection with the output lead wire from being separated from the solid electrolyte tube. Naturally, the oxygen sensor can be of one lead type not equipped with any heater and is connected by only an output lead wire. In case the oxygen sensor of the case ground type is employed and the above described metallic lead is connected to the outer surface output lead layer, it is not necessary, as shown in FIG. 12, for the end face 23 of the stopper 21 to have any radially inwardly protruded portions since the upper end of the electrode connecting portion 72, as indicated by two-dot chain line in FIG. 12, can engage almost at its entirety the lower end of the stopper 21.

What is claimed is:

1. An oxygen sensor comprising:

a tubular metal shell;

a tubular housing attached at one end thereof to said metal shell to constitute a housing assembly;

a seal member attached to another end of said tubular housing for sealingly closing the same;

a solid electrolyte tube with one open end attached to said metal shell with said open end positioned inside of said housing assembly;

electrode layers provided on inner and outer surfaces of said solid electrolyte tube;

a lead layer connected to one of said electrode layers;

a lead wire extending into said housing through said seal member and sealingly held by said seal member, said lead wire having an inner end disposed inside of said housing assembly;

a metallic lead disposed inside of said housing and connected to said inner end of said lead wire, said metallic lead having at one end thereof an electrode connecting portion having a spring property, said electrode connecting portion being fitted on one of said inner and outer surfaces of said solid electrolyte tube and held in contact with said lead layer under spring pressure; and a stopper interposed between said seal member and said open end of said solid electrolyte tube and engaged with said electrode connecting portion of said metallic lead to obstruct axial movement of said electrode connecting portion relative to said solid electrolyte tube when said lead wire is pulled outward of said housing assembly, wherein said electrode connecting portion of said metallic lead has a part-circular cross-section and an axial end face flush with a face of said open end of said solid electrolyte tube, wherein said stopper is hollow and cylindrical to allow passage of said metallic lead therethrough and has an axial end abuttingly engaged with the opened end face of said solid electrolyte tube, and wherein said electrode connecting portion of said metallic lead is fitted on said open end of said solid electrolyte tube, said stopper having at said axial end a cross-section including a four-cusp shaped central opening for passage of said metallic lead, and a solid peripheral portion for abutting engagement with said axial end face of said electrode connecting portion.

2. An oxygen sensor according to claim 1, further comprising a separator interposed between said seal member and said stopper for insulating another end of said metallic lead relative to said housing assembly, said stopper being formed integrally with said separator.

3. An oxygen sensor according to claim 1, further comprising a separator interposed between said seal member and said stopper for insulating another end of said metallic lead relative to said housing assembly, said stopper being formed separately from said separator.

* * * * *